US012376880B2

(12) United States Patent
Murray et al.

(10) Patent No.: US 12,376,880 B2
(45) Date of Patent: Aug. 5, 2025

(54) MEDICAL SYSTEMS, DEVICES, AND RELATED METHODS

(71) Applicant: Boston Scientific Scimed, Inc., Maple Grove, MN (US)

(72) Inventors: Collin Murray, Maynard, MA (US); Paul Smith, Smithfield, RI (US); Gonzalo Jose Saenz Villalobos, Alajuela (CR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 150 days.

(21) Appl. No.: 17/445,153

(22) Filed: Aug. 16, 2021

(65) Prior Publication Data

US 2022/0054166 A1 Feb. 24, 2022

Related U.S. Application Data

(60) Provisional application No. 63/066,883, filed on Aug. 18, 2020.

(51) Int. Cl.
*A61B 17/24* (2006.01)
*A61B 17/34* (2006.01)
*A61B 17/00* (2006.01)
*A61M 25/00* (2006.01)

(52) U.S. Cl.
CPC ...... *A61B 17/3423* (2013.01); *A61B 2017/00292* (2013.01); *A61B 2017/00867* (2013.01); *A61B 2017/3447* (2013.01); *A61B 2017/346* (2013.01); *A61M 25/005* (2013.01)

(58) Field of Classification Search
CPC ........... A61B 17/3423; A61B 17/0218; A61B 2017/00292; A61B 2017/00867; A61B 2017/3447; A61B 2017/346; A61B 1/00098; A61B 1/018; A61B 1/00087; A61M 25/005
USPC .................................. 606/108, 191
See application file for complete search history.

(56) References Cited

U.S. PATENT DOCUMENTS

| 8,591,399 | B2 | 11/2013 | Marescaux et al. |
| 2005/0234294 | A1 | 10/2005 | Saadat et al. |
| 2007/0135686 | A1* | 6/2007 | Pruitt, Jr. ........... A61B 17/0218 600/214 |
| 2008/0269562 | A1* | 10/2008 | Marescaux ........ A61B 1/00098 600/142 |

(Continued)

OTHER PUBLICATIONS

International Preliminary Report on Patentability and Written Opinion issued in International Application No. PCT/US2021/046135, issued Nov. 15, 2021 (13 pages).

*Primary Examiner* — Ashley L Fishback
*Assistant Examiner* — Chima U Igboko
(74) *Attorney, Agent, or Firm* — Bookoff McAndrews, PLLC (57) ABSTRACT

A medical device includes a longitudinal portion with one or more tubes, a distal portion with one or more arms, and one or more actuation mechanisms. The one or more arms each includes an arm lumen. Each arm lumen is connected to a respective tube, and at least one of the longitudinal portion and the distal portion is configured to be coupled to a distal end of an insertion device. The one or actuation mechanisms are movable to transition one or more arms from a closed configuration to an open configuration.

20 Claims, 4 Drawing Sheets

(56) References Cited

U.S. PATENT DOCUMENTS

| | | | |
|---|---|---|---|
| 2010/0298642 A1* | 11/2010 | Trusty | A61B 1/00135 600/114 |
| 2013/0237760 A1* | 9/2013 | Adams | A61B 1/00135 600/146 |
| 2016/0038133 A1* | 2/2016 | Smith | A61B 17/320016 600/204 |
| 2018/0303317 A1 | 10/2018 | Matthison-Hansen | |

* cited by examiner

MEDICAL SYSTEMS, DEVICES, AND RELATED METHODS

CROSS-REFERENCE TO RELATED APPLICATIONS

This application claims the benefit of priority from U.S. Provisional Application No. 63/066,883, filed on Aug. 18, 2020, which is incorporated by reference herein in its entirety.

TECHNICAL FIELD

Various aspects of this disclosure generally relate to medical systems, devices, and methods for grasping, cutting, or otherwise manipulating or treating tissue or other material within a body. In particular, aspects of the disclosure relate to medical systems, devices, and methods for performing a medical procedure using, in some embodiments, one or more end effectors capable of being inserted into the body to treat a treatment site from a number of angles and/or provide stabilization or leverage during the treatment.

BACKGROUND

A wide variety of medical techniques and instruments have been developed for diagnosis and/or treatment within a patient's body, such as within a patient's gastrointestinal (GI) tract. Endoscopic sub-mucosal dissection (ESD), endoscopic sub-mucosal resection (ESR), mucosal resection (EMR), polypectomy, mucosectomy, etc., are minimally invasive treatment methods for both malignant and non-malignant lesions. Endoscopic medical procedures, such as, for example, ESR, may be used to excise sessile adenomas or other unwanted tissue (e.g., tumors attached to a bodily surface) from the surface of an anatomical lumen (e.g., stomach, esophagus, colon, etc.). Such procedures often require the resection of one tissue plane while leaving an underlying tissue plane intact. Commonly, snares are used during such medical procedures, for resecting tissue from a target site. However, many conventional snares operate in only one degree of freedom, and manipulation of the snare is dependent on the tip deflection of an endoscope or other device used for insertion into the patient. Further, the distal end of the endoscope or other device may require additional stabilization and/or leverage during the treatment in order for the user to have enough traction to perform the treatment and/or block other tissue or material from interfering with the treatment. In some aspects, additional stabilization and/or leverage may be required on one or more, but not all, sides of the endoscope, for example, depending on the direction of a cut, angle of approach, details of the treatment site, etc.

Delivering an endoscope to a patient may also require an insertion sheath or other additional device to help ensure an atraumatic insertion. Additionally, repositioning an end effector relative to the endoscope and/or treatment site may require the user to remove one or more of the end effector or the endoscope from the patient. These concerns may increase the duration, costs, and risks of the medical procedure. The devices and methods of this disclosure may rectify some of the deficiencies described above or address other aspects of the art.

SUMMARY

Examples of this disclosure relate to, among other things, systems, devices, and methods for performing one or more medical procedures with the medical systems and devices. Each of the examples disclosed herein may include one or more of the features described in connection with any of the other disclosed examples.

In one example, a medical device may include a longitudinal portion with one or more tubes, a distal portion with one or more arms, and one or more actuation mechanisms. The one or more arms each may include an arm lumen. Each arm lumen may be connected to a respective tube, and at least one of the longitudinal portion and the distal portion may be configured to be coupled to a distal end of an insertion device. The one or actuation mechanisms may be movable to transition one or more arms from a closed configuration to an open configuration.

The medical device may include one or more of the following features. In the closed configuration, the arm lumens may not be exposed from the distal portion, and in the open configuration, the arm lumens may be exposed from the distal portion. The tubes and the arm lumens may be aligned and configured to receive and deliver one or more end effectors out of the arm lumens. The arm lumens may have a curvature of approximately 0 to 60 degrees relative to a longitudinal axis of the medical device, when the medical device is in the open configuration. The one or more arms may include four arms that form a substantially round shape in the closed configuration. In the closed configuration, the four arms may form a central opening at a distal end of the round shape. The actuation mechanism may be one or more wires positioned within the one or more tubes. The one or more wires may be connected to proximal portions of the one or more arms.

The medical device may further include a coupling portion that surrounds a portion of the one or more tubes and/or a portion of the one or more arms. The medical device may further include a ring coupled to or formed with the one or more arms, and the ring may be further coupled to the coupling portion. The one or more arms may include one or more spring arms. Each spring arm may pivot at a proximal end of the spring arm, and the actuation mechanism may include an over-tube configured to slide over a proximal portion of the one or more arms, a push rod configured to abut a proximal portion of the one or more spring arms, or a curved portion that is coupled to a slot in the one or more spring arms. The coupling portion may include a longitudinal guide channel. The actuation mechanism may be a slat that is movably positioned within the guide channel and may be configured to abut and manipulate a proximal portion of the one or more arms. The medical device may further include one or more partially circumferential shrouds coupled to the one or more arms. The one or more actuation mechanisms may include a first wire and a second wire. The first wire may be movable relative to the one or more arms and may be extendable through the one or more arms to form a rail, and the second wire may be fixed relative to the one or more arms and movable to extend the one or more arms along the rail. The one or more tubes may include a coiled wire.

In another example, a medical system may include an insertion device including one or more lumens and a medical device. The medical device may be configured to be coupled to a distal end of the insertion device. The medical device may include one or more arms at a distal end, one or more tubes connected to a proximal end of each of the one or more arms, and one or more wires passing through the one or more tubes and connected to a portion of each of the one or more arms. Movement of the one or more wires may transition the one or more arms from a first configuration to a second configuration, and the arms may be farther away from a longitudinal axis of the insertion device in the second configuration.

The medical system may include one or more of the following features. The one or more wires may include a first wire and a second wire. The first wire may be movable to extend beyond the one or more arms to form a rail, and the one or more arms may be movable along the rail based on the movement of the second wire. The first wire may be formed of a shape memory metal.

In yet another aspect, a medical device may include one or more tubes, one or more arms, and one or more actuation mechanism. The one or more tubes may be configured to be coupled to a radial exterior of an insertion device. The one or more arms may be configured to be coupled to a distal end of the insertion device, and the one or more arms may be biased toward an open configuration. The one or more actuation mechanisms may be movable to transition the one or more arms between the open configuration and a closed configuration.

The medical device may include one or more of the following features. The medical device may further include a coupling portion that surrounds a portion of the one or tubes and may include a guide channel configured to receive a portion of the actuation member. The one or more arms may be connected to a ring portion that is configured to couple the one or arms to the coupling portion, and the ring portion may include a cylindrical projection configured to be inserted into an opening in the coupling portion.

In another example, a method of treatment may include delivering a medical device to a treatment site. The medical device may include a longitudinal portion and a distal portion. The longitudinal portion may include one or more tubes. The distal portion may include one or more arms that are moveable between a closed configuration and an open configuration. The one or more arms may each include an arm lumen. Each arm lumen may be connected to a respective tube. During the delivery of the medical device to the treatment site, the one or more arms may be in the closed configuration. Once at the treatment site, the method may include transitioning the one or more arms from the closed configuration to the open configuration. Then, the method may include delivering an instrument or end effector through one tube and one arm lumen to extend the instrument or end effector distally out of the arm lumen. The method may further include performing a procedure at the treatment site with the instrument or end effector. Then, the method may include at least partially retracting the instrument or end effector, and transitioning the one or more arms from the open configuration to the closed configuration.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIG. 1A illustrates a perspective view of an exemplary medical system in a first configuration.

DETAILED DESCRIPTION

The terms "proximal" and "distal" are used herein to refer to the relative positions of the components of an exemplary medical system and exemplary medical devices. When used herein, "proximal" refers to a position relatively closer to the exterior of the body or closer to a medical professional using the medical system or medical device. In contrast, "distal" refers to a position relatively further away from the medical professional using the medical system or medical device, or closer to the interior of the body. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/—10% of a stated value.

Examples of this disclosure include systems, devices, and methods for facilitating and/or improving the efficacy, efficiency, and/or safety of a medical procedure. Embodiments of the disclosure may relate to systems, devices, and methods for performing various medical procedures and/or treating portions of the large intestine (colon), small intestine, cecum, esophagus, any other portion of the gastrointestinal tract, and/or any other suitable patient anatomy. Various embodiments described herein include single-use or disposable medical devices. Some aspects of the disclosure may be used in performing an endoscopic, arthroscopic, bronchoscopic, ureteroscopic, colonoscopic, or other type of procedure. For example, the disclosed aspects may be used with duodenoscopes, bronchoscopes, ureteroscopes, colonoscopes, catheters, diagnostic or therapeutic tools or devices, or other types of medical devices. One or more of the elements discussed herein could be metallic, plastic, or include a shape memory metal (such as nitinol), a shape memory polymer, a polymer, or any combination of biocompatible materials.

Reference will now be made in detail to examples of the disclosure described above and illustrated in the accompanying drawings. Wherever possible, the same reference numbers will be used throughout the drawings to refer to the same or like parts. It is noted that one or more aspects of the medical systems or devices discussed herein may be combined and/or used with one or more aspects of other medical systems or devices discussed herein.

Figure 1A:
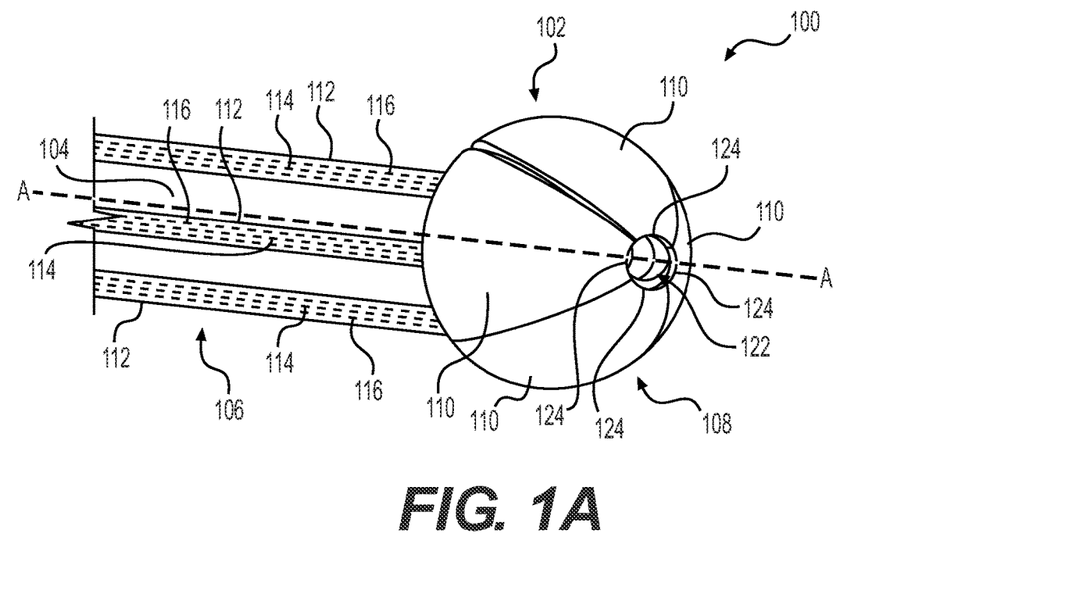
Figure 1B:
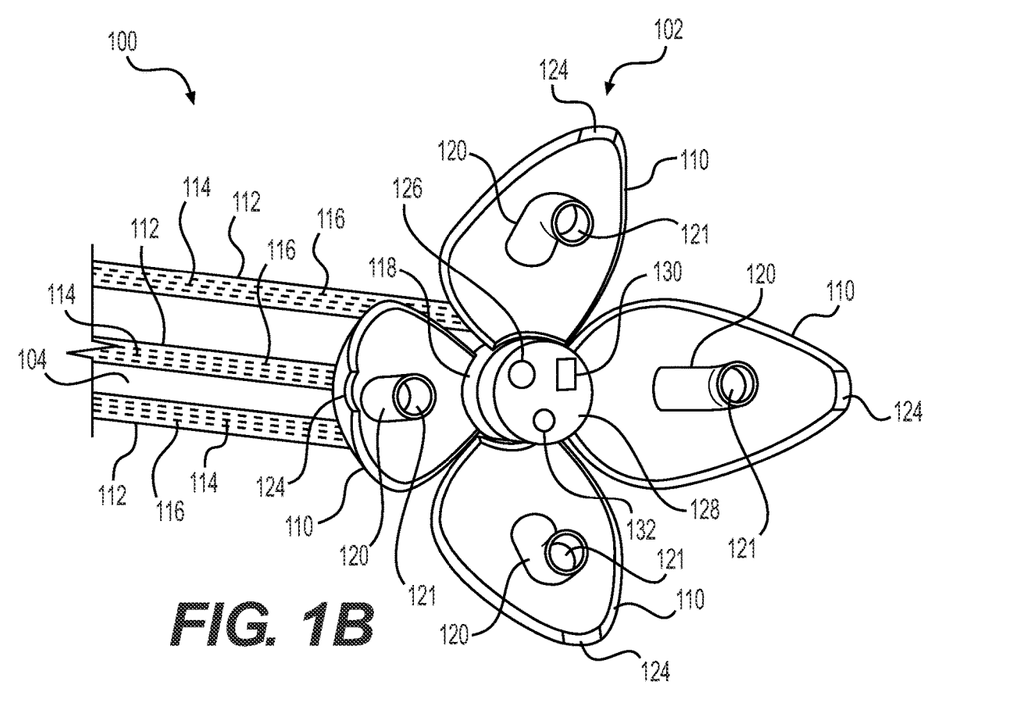
FIG. 1B illustrates a perspective view of the exemplary medical system in a second configuration, according to aspects of this disclosure.

FIGS. 1A and 1B illustrate perspective views of an exemplary medical system 100 that includes a medical device 102 and an insertion device 104. Medical device 102 may be coupled to or otherwise positioned on a distal end of insertion device 104, for example, via a press-fit, friction fit, snap fit, adhesive, etc. Insertion device 104 may be, for example, an endoscope, duodenoscope, bronchoscope, ureteroscope, colonoscope, catheter, diagnostic or therapeutic tool or device, or other types of insertion or medical devices to access, diagnose, and/or treat tissue. For example, medical device 102 may be an over-the-scope device, in which a user may position medical device 102 over a distal end of the insertion or medical device before a medical procedure.

FIG. 1A illustrates medical device 102 in a closed configuration, and FIG. 1B illustrates medical device 102 in an open configuration. For example, as discussed herein, medical device 102 may be delivered to a treatment site in the closed configuration, and then transitioned to the open configuration to treat the treatment site. Medical device 102 includes a longitudinal portion 106 and a distal end portion 108. As shown in FIGS. 1A and 1B, distal end portion 108 includes a plurality of arms 110. Arms 110 may be movable between, at least, a substantially closed configuration (FIG. 1A) and a substantially open configuration (FIG. 1B).

Longitudinal portion 106 may include a plurality of tubes 112, which are configured to be coupled to a radial exterior of insertion device 104. Each tube 112 may be connected to a proximal portion of one arm 110. For example, as shown in FIGS. 1A and 1B, medical device 102 may include four tubes 112 and four arms 110. Although not shown, medical device 102 may include any number of tubes 112 and arms 110. For example, medical device 102 may include two tubes 112 and two arms 110, three tubes 112 and three arms 110, five tubes 112 and five arms 110, etc. Additionally, in some aspects, medical device 102 may include differing numbers of tubes 112 and arms 110. For example, medical device 102 may include four tubes 112 and two arms 110, may include two tubes 112 and four arms 110, etc. Tubes 112 may extend along an exterior of insertion device 104, for example, parallel to a longitudinal axis A of insertion device 104. Tubes 112 may extend along most or an entire length of insertion device 104, for example, connecting to a handle or other user interface (not shown) at a proximal end of insertion device 104. Furthermore, one or more portions of tubes 112 and/or arms 110 may be coupled to one or more portions of insertion device 104. For example, one or more portions of tubes 112 or arms 110 may be coupled to one or more portions of insertion device 104 via a press-fit, friction fit, snap fit, adhesive, etc.

Figure 3:
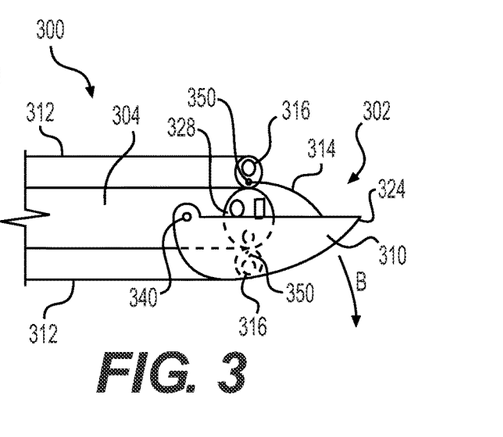
FIG. 3 illustrates a side view of yet another exemplary medical system, according to aspects of the disclosure.

Tubes 112 may each include an actuation mechanism, for example, a wire 114, and a channel 116. For example, each wire 114 may be movably positioned within each tube 112, and may be connected to a portion of a respective arm 110. For example, each wire 114 may be positioned within a respective channel 116 of each tube 112. Alternatively, as shown in FIG. 3 and discussed below, each wire 114 may be movably positioned within a wire channel or lumen in each tube 112 that is separated from channel 116 in each tube 112. Proximal movement of one or more wires 114 may open one or more arms 110, as in FIG. 1B, and distal movement of one or more wires 114 may close one or more arms, as in FIG. 1A. In one aspect, arms 110 may be biased toward one configuration, for example, with an internal spring or other biasing device. For example, arms 110 may be biased toward the closed configuration shown in FIG. 1A, and wires 114 may be pulled proximally to transition arms 110 to the open configuration shown in FIG. 1B. Alternatively, arms 110 may be biased toward the open configuration shown in FIG. 1B, and wires 114 may be pushed or advanced distally to transition arms 110 to the closed configuration shown in FIG. 1A. Wires 114 may be configured to be moved together, for example, to control the opening or closing of distal portion 108, or wires 114 may be individually movable, for example, to control the opening or closing of individual arms 110. In one aspect, wires 114 may be individually movable, for example, to allow the user to selectively manipulate portions of distal portion 108 for one or more different angles of approach to a treatment site. Additionally, one or more wires 114 may be moved to control one or more arms 110, for example, to push, pull, block, or otherwise manipulate tissue or other material at the treatment site, for example, to provide stabilization, leverage, etc. for medical system 100 relative to tissue or other material at the treatment site.

Distal portions of tubes 112 and/or proximal portions of arms 110 may be coupled via a connection portion 118. For example, connection portion 118 may be a generally circular or cylindrical element, for example, shaped like a ring, that connects distal portions of tubes 112 and/or proximal portions of arms 110, and that couples medical device 102 to a portion of insertion device 104. Furthermore, if arms 110 are connected to connection portion 118, arms 110 may be pivotally connected, for example, in order to allow arms 110 to pivot relative to connection portion 118.

Although not shown, each channel 116 may include a substantially circular cross-section within each tube 112. Each wire 114 may extend through the circular cross-section of channel 116. Alternatively, each channel 116 may include an outward indentation, for example, radially outward from a longitudinal axis of each channel 116, and each wire 114 may be positioned and movable within the outward indentation. In any of these aspects, each channel 116 may be sized to receive one or more end effectors (e.g., a snare, a clip, a grasper, a knife, a laser fiber, etc.) or an illumination or visualization device to extend through channel 116 and out of a portion of the corresponding arm 110. Moreover, although not shown, tubes 112 may be formed by bores through a sheath or otherwise enclosed by or surrounded by a sheath.

Arms 110 may include rounded, curved shapes, for example, such that distal portion 108 forms a substantially spherical, ovoid, or tulip-shaped arrangement in the closed configuration shown in FIG. 1A. Each arm 110 may form approximately 90 degrees (relative to longitudinal axis A) of the substantially spherical, ovoid, or tulip-shaped arrangement. As mentioned a proximal portion of each arm 110 is connected to a respective wire 114, such that movement of wire 114 may control the position of arm 110.

Moreover, each arm 110 includes an arm tube 120 that forms an arm channel 121 therein. Arm tube 120 may extend from an interior portion of arm 110, as shown in FIG. 1B, and each arm channel 121 may be connected to channel 116 of a corresponding tube 112. In this aspect, one or more end effectors (e.g., a snare, a clip, a grasper, a knife, a laser fiber, etc.) or an illumination or visualization device may be delivered to the treatment site through one tube 112 and out of arm channel 121 of one arm tube 120. For example, in the closed configuration, arm tubes 120 may not be exposed from distal portion 108, and in the open configuration, arm tubes 120 are exposed from distal portion 108. As shown in FIG. 1B, each arm tube 120 may have a curvature, for example, a gradual curvature toward longitudinal axis A of insertion device. In this aspect, the curvature of each arm tube 120 may approximate a curvature of each arm 110. In one example, each arm tube 120 may have a curvature of approximately 0 to 60 degrees, for example, approximately 45 degrees. In this aspect, the curvature of each arm tube 120 results in the distal opening of arm channel 121 facing distally and radially inward. In other aspects, if arm tube 120 is not curved (e.g., has a curvature of approximately 0 degrees), distal opening of arm channel 121 may face distally, for example, to deliver one or more end effectors straight toward or into tissue.

Although not shown and as discussed below, medical device 102 may include two, three, five, six, etc. arms 110. Arms 110 may form a spherical, ovoid, or tulip-shaped arrangement in the closed configuration. Moreover, arms 110 may include even sizing, or uneven sizing, for example, each arm 110 may be substantially the same size and shape, or one or more arms 110 may include a different size and/or shape than one or more other arms 110. In the closed configuration, arms 110 may form a full circumference (no spaces between adjacent arms), or arms 110 may not form a full circumference, for example, with spaces between lateral side portions of adjacent arms 110. Arms 110 may be formed of plastic, metal, or another biocompatible material.

Additionally, in this aspect, medical device 102 may include as many tubes 112, with corresponding wires 114 and channels 116, as necessary to have one tube 112 connected to each arm 110. Alternatively, medical device 102 may include one tube 112, one wire 114, and a plurality of arms 110. In this aspect, the movement of wire 114 may control the position of all of the plurality of arms 110. For example, the plurality of arms 110 may be connected at connection portion 118, and the one wire 114 may be configured to actuate the plurality of arms 110 by pivoting, rotating, or otherwise manipulating connection portion 118. Alternatively, one wire 114 may extend through one tube 112, and then branch out into several distal portions, with each of the distal portions connected to one arm 110, such that movement of wire 114 controls the position of each of the plurality of arms 110.

As shown in FIG. 1A, when in the closed configuration, arms 110 may abut each other to form closed sides, but form a central opening 122, for example, formed by a space between distal end portions 124 of arms 110. Central opening 122 may at least partially align with one or more lumens 126 (FIG. 1B) in insertion device 104. In this aspect, one or more end effectors (e.g., a snare, a clip, a grasper, a knife, a laser fiber etc.), an illumination or visualization device, suction, and/or irrigation may be delivered through one or more lumens of insertion device 104 and out of central opening 122 with arms 110 in the closed configuration, for example, to extend beyond distal portion 108. Then, as shown in FIG. 1B, transitioning to the open configuration causes arms 110 to pivot radially outward such that adjacent arms 110 separate and expose a greater portion of insertion device 104. Furthermore, as discussed below, for example, with respect to FIG. 2, arms 110 may not enclose distal end 128 of insertion device 104. For example, in these aspects, arms 110 may be positioned on insertion device 104 at positions proximal to distal end 128 such that, when arms 110 are in the closed configuration, arms 110 surround a portion of the exterior of insertion device 104 while leaving distal end 128 exposed.

Insertion device 104 may be a substantially elongate member, and may include one or more lumens 126, for example, extending through insertion device 104 longitudinally from a proximal end (not shown) to a distal end 128. Additionally, in some aspects, insertion device 104 may include one or more illumination devices 130 (e.g., a light, LED, light fiber) and/or one or more visualization devices 132 (e.g., a camera). Furthermore, insertion device 104 may be deflectable, for example, via one or more controls on a proximal handle (not shown).

In some aspects, medical device 102 and insertion device 104 may be longitudinally movable relative to one another. For example, the coupling between medical device 102 and insertion device 104 may allow for one or more portions of medical device 102 to be extended distally or retracted proximally relative to insertion device 104. Alternatively or additionally, the coupling between medical device 102 and insertion device 104 may allow for insertion device 104 to be extended distally or retracted proximally relative to medical device 102.

Figure 2:
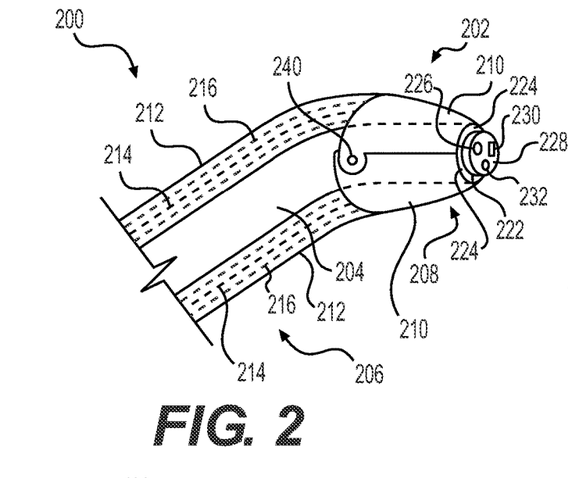
FIG. 2 illustrates a side view of another exemplary medical system, according to aspects of this disclosure.

FIG. 2 illustrates an alternative example, according to the disclosure. FIG. 2 illustrates similar elements to medical system 100 shown by 100 added to the reference numbers. As shown, a medical system 200 includes a medical device 202 and an insertion device 204.

Medical device 202 includes a longitudinal portion 206 and a distal portion 208. Longitudinal portion 206 includes tubes 212, and distal portion 208 includes arms 210. As shown, distal portion 208 may include two arms 210, for example, coupled via a hinge 240. As discussed above, one or more wires 214 may be positioned in channels 216 of respective tubes 212 and be coupled to respective arms 210 to control the configuration of arms 210. As discussed, arms 210 may be biased toward a certain configuration (e.g., the closed configuration), and wires 214 may be movable to transition the configuration of arms 210. Medical device 202 may be coupled to a distal portion of insertion device 204, as discussed above. For example, although not shown, arms 210 may be connected to insertion device 204 via a connection portion. Moreover, each arm 210 may include an arm tube (not shown) connected to a respective tube 212 to deliver one or more end effectors to the treatment site.

As shown in FIG. 2, in the closed configuration of arms 210, a central opening 222 may be sized to receive and/or expose distal end 228 of insertion device 204. In this aspect, distal end 228 may be positioned slightly distally beyond, aligned with, or slightly proximally within distal end portions 224 of arms 210. As shown, lumen 226, illumination device 230, and visualization device 232 of insertion device 204 may be substantially unobstructed by arms 210, even in the closed configuration. Additionally, the shape of arms 210 in the closed configuration may help form an atraumatic tip, for example, during delivery to the treatment site and/or during repositioning.

FIG. 3 illustrates an alternative example, according to the disclosure. FIG. 3 illustrates similar elements to medical system 100 shown by 200 added to the reference numbers. As shown, a medical system 300 includes a medical device 302 and an insertion device 304. Medical device 302 may be coupled to a distal portion of insertion device 304, as discussed above.

Similar to medical device 202, medical device 302 includes two arms 310 that are connected via a hinge 340 and are controllable by wires 314 positioned within tubes 312. For clarity, however, only one arm 310 is shown in FIG. 3. As shown in FIG. 3, distal end 328 of insertion device 304 is positioned within distal end portions 324 of arms 310. In this aspect, arms 310 do not form a central opening, and distal end portion 328 of insertion device 304 is fully enclosed proximally within arms 310 in the closed configuration.

Additionally, each tube 312 includes a wire channel 350, for example, separated from channel 316. In this aspect, one wire 314 may be positioned in each wire channel 350. Moreover, each wire 314 may be connected to an opposite arm 310. For example, as shown in FIG. 3, which only illustrates one arm 310 and one wire 314 for clarity purposes, a wire 314 may pass through wire channel 350 of a first tube 312, and a distal end of wire 314 may be connected to a portion of arm 310 that is adjacent to a second tube 314. In this aspect, a user may distally extend wire 314 in order to urge arm 310 toward an open configuration (arrow B), and a user may proximally retract wire 314 in order to urge arm 310 toward a closed configuration. Accordingly, the expansion of arm 310 may be controlled by the position of wire 314, for example, to control the leverage against tissue or other material at the treatment site and/or to provide different angles of approach to the treatment site for one or more end effectors. Additionally, as discussed above, the closed configuration and/or the shape of arms 310 may help to protect distal end 328 of insertion device 304 and/or help to form an atraumatic tip, for example, during delivery to the treatment site and/or during repositioning.

Figure 4:
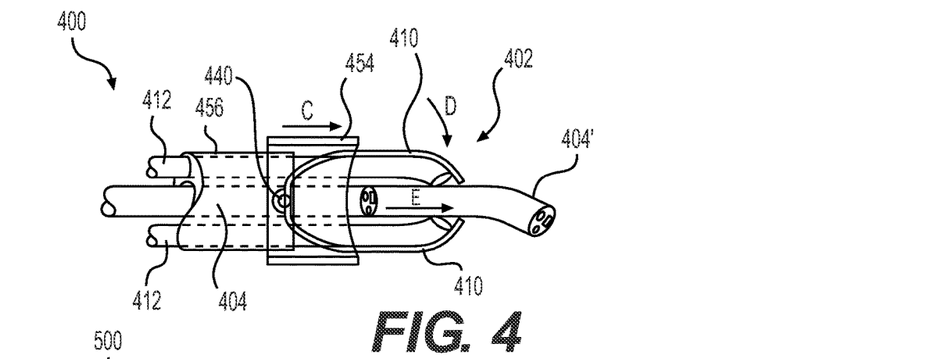
FIG. 4 illustrates a side view of an exemplary medical system, according to aspects of this disclosure.

FIG. 4 illustrates an alternative example, according to the disclosure. FIG. 4 illustrates similar elements to medical system 100 shown by 300 added to the reference numbers. As shown, a medical system 400 includes a medical device 402 and an insertion device 404.

Medical device 402 includes one or more arms 410 and one or more tubes 412, as discussed above. Additionally, arm(s) 410 may include a hinge 440, and if medical device 402 includes a plurality of arms 410, the arms 410 may be connected at hinge 440. Distal portions of arms 410 may curve radially inward, for example, toward the longitudinal axis of insertion device 404. Additionally, tubes 412 may also curve radially inward, for example, toward the longitudinal axis of insertion device 404. The curvature of arms 410 and/or tubes 412 may help deliver one or more end effectors at an appropriate angle of approach toward a treatment site.

In one aspect, arms 410 may be formed by spring arms, so that arms 410 may be biased toward an expanded or open configuration. For example, arms 410 may be formed with a specific shape, curvature, or configuration, and moving arms 410 (e.g., relative to a pivot point) from that shape or curvature may result in arms 410 being biased (e.g., exerting a force) toward the original specific shape, curvature, or configuration. Nevertheless, medical device 402 may also include an actuation member 454. Actuation member 454 may be a cylindrical element that is longitudinally movable relative to at least a portion of arms 410. As shown, actuation member 454 may be formed by an over-tube. Accordingly, actuation member 454 may be moved distally (arrow C), for example, slid distally over an exterior portion of arms 410, in order to urge arms 410 toward an at least partially closed configuration (arrow D), as shown in FIG. 4. Moreover, actuation member 454 may be moved further distally to urge arms 410 to a fully closed configuration, for example, in which insertion device 404 is fully enclosed by arms 410. Although not shown, actuation member 454 may be moved proximally to allow arms 410 to bias outward toward an at least partially opened configuration.

In these aspects, actuation member 454 may be controlled by at a proximal portion of medical system 400. For example, actuation member 454 may extend proximally to a location outside of the patient such that the user may manipulate actuation member 454, for example, manually. Alternatively, actuation member 454 may be connected to a drive wire or other component that extends proximally, for example, to a handle or other user interface such that the user may indirectly manipulate actuation member 454.

Medical device 402 may be coupled to a distal portion of insertion device 404, as discussed above. In one aspect, as discussed above, one or more tubes 412 may be coupled to insertion device 404. As shown in FIG. 4, tubes 412 may be coupled to insertion device 404 and/or extend through or otherwise be surrounded by a coupling portion 456. Additionally, insertion device 404 may be movable relative to coupling portion 456 and medical device 402, for example, as shown by arrow E, to extend insertion device 404 distally beyond medical device 402, shown as insertion device 404'. Arms 410 may be fully closed to help protect insertion device 404 and/or form an atraumatic tip, for example, during delivery and/or repositioning of medical system 400. Additionally, arms 410 may be partially opened, as shown in FIG. 4, for example, to allow for a portion of insertion device 404 to be exposed and/or extended through arms 410. Furthermore, arms 410 may be fully opened to provide a number of angles of approach for one or more end effectors to treat the treatment site, as discussed above.

Figure 5:
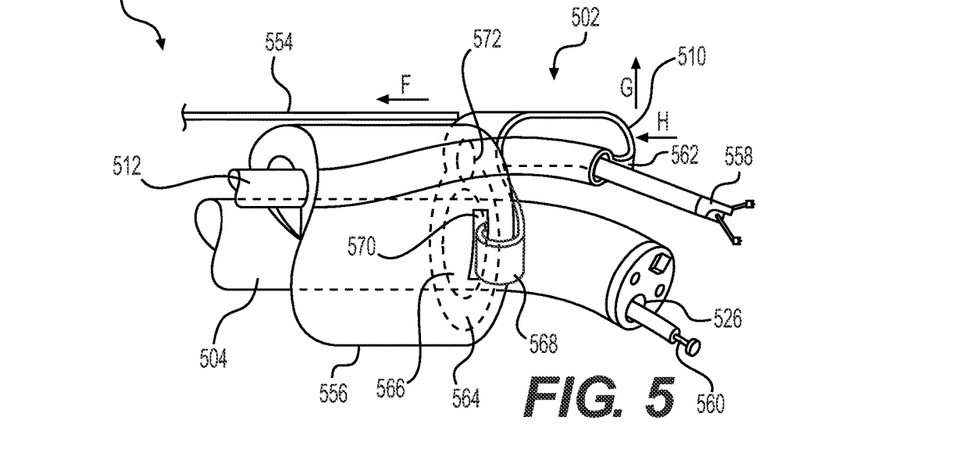
FIG. 5 illustrates a perspective view of another exemplary medical system, according to aspects of this disclosure.

FIG. 5 illustrates an alternative example, according to the disclosure. FIG. 5 illustrates similar elements to medical system 100 shown by 400 added to the reference numbers. As shown, a medical system 500 includes a medical device 502 and an insertion device 504.

Medical system 500 is similar to medical system 400 in that one or more tubes 512 may be coupled to one or more arms 510, and may be coupled to insertion device 504 via a coupling portion 556. Arm 510 may be formed by a spring arm, as discussed above, such that moving arm 510 (e.g., relative to a pivot point) from the original shape, curvature, or configuration results in arm 510 being biased and/or exerting a force toward the original shape or curvature. As shown, one or more end effectors 558 (e.g., a grasper) may be delivered through tube 512, and one or more end effectors 560 (e.g., an ESD knife) may be delivered through a lumen 526 of insertion device 504. It is noted that tube 512 may extend to a distal portion of arm 510, or tube 512 may be aligned or otherwise connected to an arm tube connected to arm 510, as discussed herein. For example, tube 512 may be coupled to, for example, a distal portion of arm 510 via a distal connection 562, for example, a hooked or curved portion of arm 510 that may be hooked around, received within, or otherwise coupled to a distal portion of tube 512. For example, distal connection 562 may extend proximally of the distal end of arm 510. Distal connection 562 may be connected (e.g., via an adhesive) to a distal end portion of tube 512. In another aspect, distal connection 562 may include a circular projection (not shown) that may be received within the distal portion of tube 512 to couple tube 512 to arm 510. Alternatively, distal connection 562 may include a circular projection (not shown) that may surround the distal portion of tube 512 to couple tube 512 to arm 510. Additionally, one or more actuation members 554 may be connected to a portion of arm 510. In this aspect, however, actuation member 554 may be a push rod or a strut. Nevertheless, actuation member 554 may also be an over-tube, as discussed above.

In addition, arm 510 may be integrally formed with or otherwise coupled to a ring portion 564 that has an annular, ring shape. In this aspect, arm 510 extends distally of ring portion 564 and is radially outward of ring portion 564. Ring portion 564 may allow for insertion device 504 to pass through a central passage 566 of ring portion 564. Ring portion 564 may be positioned distal to coupling portion 556. For example, ring portion 564 may be coupled to a distal portion of coupling portion 556 via a hooked portion 568 of ring portion 564 extending through or at least partially into a slot, groove, or opening 570 in coupling portion 556. Although not shown, medical system 500 may include a plurality of hooked portions 568 and openings 570 to couple ring portion 564 to coupling portion 556. Moreover, coupling portion 556 may include a through-hole 572, for example, to allow a distal portion of tube 512 to pass through and connected to arm 510.

As shown in FIG. 5, actuation member 554 may attached to or abut a proximal portion of arm 510, for example, at a location radially outward of through-hole 572 and/or at a bent junction between arm 510 and ring portion 564. Actuation member 554 may be moved proximally (arrow F) to allow arm 510 to bias outward (arrow G) toward an at least partially open configuration. Furthermore, coupling portion 556 may be retracted proximally, and because arm 510 is connected to coupling portion 556 via ring portion 564, proximal retraction of coupling portion 556 may also retract arm 510 (arrow H). Moreover, although not shown, but as discussed above with respect to FIG. 4, actuation member 554 may be moved distally to urge arm 510 toward an at least partially closed configuration or a fully closed configuration. As discussed above, such movement may help to protect insertion device 504 and/or to form an atraumatic tip, while also helping to provide a number of angles of approach for one or more end effectors to treat the treatment site.

Figure 6:
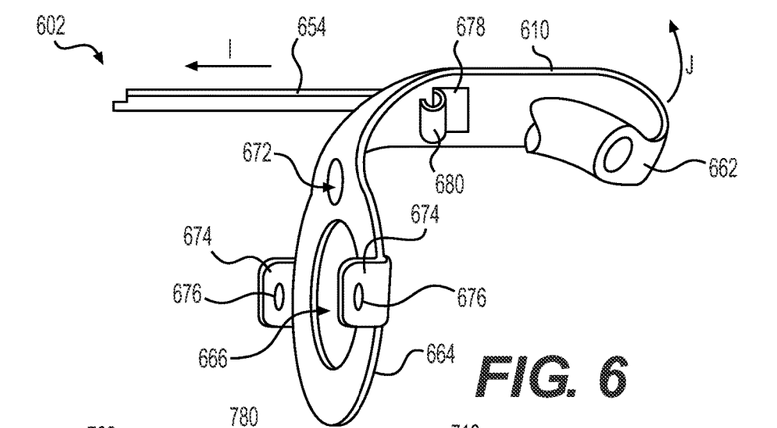
FIG. 6 illustrates a perspective view of a portion of an exemplary medical device, according to aspects of this disclosure.

FIG. 6 illustrates an alternative example, according to the disclosure. FIG. 6 illustrates similar elements to medical device 102 shown by 500 added to the reference numbers. As shown, a medical device 602 includes an arm 610 that may be formed with or otherwise coupled to an annular ring portion 664. Arm 610 may be coupled to a tube (not shown) for example, via distal connection 662. For example, as discussed above, a distal connection 662 may be coupled to a distal portion of the tube via an adhesive or other coupling mechanism. In one aspect, a portion of distal connection 662 may be positioned within the distal opening of the tube, or in another aspect, the tube may fit within a lumen of distal connection 662. The tube may also extend through a through-hole 672 in ring portion 664. Ring portion 664 may allow for the insertion device to pass through a central passage 666 of ring portion 664. Additionally, ring portion 664 may include one or more proximal extensions 674, for example, on opposing sides of ring portion 664. Extensions 674 may include holes 676, which may receive a pin, tab, tack, screw, or other coupling element to connect ring portion 664 to a coupling portion or the insertion device. Alternatively, although not shown, ring portion 664 may include one or more hooked portions, as discussed with respect to FIG. 5.

Additionally, arm 610 and/or ring portion 664 may include a slot 678, which may receive a portion of an actuation member 654. For example, actuation member 654 may include a curved portion 680 at a distal portion. At least a portion of arm 610 is flexible. In this aspect, actuation member 654 may be pulled proximally (arrow I), which causes at least a portion of arm 610 to expand outwardly (arrow J) away from the longitudinal axis. In this aspect, arm 610 may pivot about a proximal end of arm, for example, at or near a junction of arm 610 with ring portion 664, and/or near through-hole 672. Although not shown, actuation member 654 may be extended distally, which may cause at least a portion of arm 610 to pivot and contract inwardly toward the longitudinal axis, as discussed above. Additionally, arm 610 may or may not include a spring arm or otherwise be biased toward an open configuration, and the action of actuation member 654 may control the position of arm 610, and thus the position of a tube or end effector connected to arm 610. In these aspects, medical device 602 may help to protect the insertion device and/or to form an atraumatic tip, while also helping to provide a number of angles of approach for one or more end effectors to treat the treatment site.

Figures 7, 8:
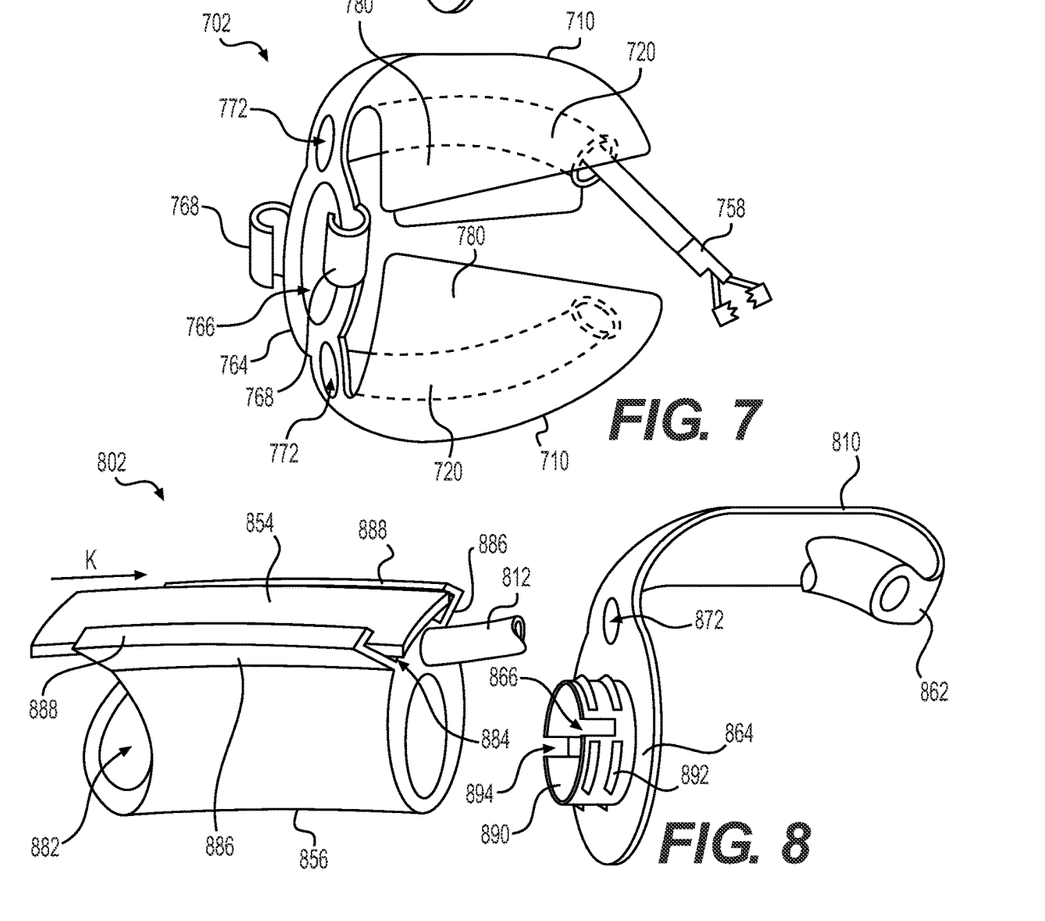
FIG. 7 illustrates a perspective view of a portion of another exemplary medical device, according to aspects of this disclosure.
FIG. 8 illustrates a partially exploded view of an exemplary medical system, according to aspects of this disclosure.

FIG. 7 illustrates an alternative example, according to the disclosure. FIG. 7 illustrates similar elements to medical device 102 shown by 600 added to the reference numbers. As shown, a medical device 702 includes one or more arms 710 that may be formed with or otherwise coupled to a ring portion 764. Each arm 710 may be coupled to a corresponding tube (not shown) for example, via a respective through-hole 772 in ring portion 764. Additionally, ring portion 764 may include one or more hooked portions 768. Alternatively, although not shown, ring portion 764 may include one or more proximal extensions, as discussed with respect to FIG. 6. Ring portion 764 may allow for the insertion device to pass through a central passage 766.

Medical device 702 may include two or more arms 710 that may each include a shroud 780. Each shroud 780 may be partially circumferential, and may help to form a spherical, ovoid, or tulip-shaped arrangement with arms 710 in a closed configuration. Additionally, arms 710 may include arm tubes 720 to allow for an end effector 758 to be delivered from the tube, through arm tube 720, and out of medical device 702 to the treatment site. Alternatively, arms 710 may be coupled to a distal portion of the tubes, as discussed herein. In these aspects, medical device 702 may help to protect the insertion device and/or to form an atraumatic tip, while also helping to provide a number of angles of approach for one or more end effectors 758 to treat the treatment site.

FIG. 8 illustrates an alternative example, according to the disclosure. FIG. 8 illustrates similar elements to medical device 102 shown by 700 added to the reference numbers. As shown, a medical device 802 may be coupled to an insertion device (not shown). Medical device 802 includes one or more arms 810 that may be formed with or otherwise coupled to a ring portion 864. Arms 810 may be coupled to a tube 812 for example, via a through-hole 872 in ring portion 864 and/or a distal connection 862. Ring portion 864 may allow for the insertion device to pass through a central passage 866.

Additionally, medical device 802 may include a coupling portion 856, which includes a central opening 882 to receive a portion of the insertion device. Coupling portion 856 also includes a guide channel 884, for example, to receive a portion of an actuation member 854. For example, guide channel 884 may be formed by two radial wings 886, which may each include end notches 888 that face each other. In this aspect, actuation member 854 may be movable (e.g., slidable) relative to coupling portion 856 through guide channel 884, and at least partially retained within guide channel 884. Furthermore, ring portion 864 may include an attachment portion 890 that, for example, includes a cylindrical projection extending in an opposite direction than arm 810, i.e., proximally. Attachment portion 890 may include ribs or radial extensions 892, for example, along a radial exterior of attachment portion 890. Moreover, attachment portion 890 may also include one or more gaps 894. In this aspect, attachment portion 890 may be inserted into central opening 882 of coupling portion 856 to couple ring portion 864 to coupling portion 856. Radial extensions 892 and/or gaps 894 may help the user to couple or uncouple ring portion 864 to coupling portion 856, for example, with attachment portion 890 being positioned between a radial exterior of an insertion device and a radial interior of central opening 882. For example, gaps 894 may allow some flexibility inward for attachment portion 890 during insertion into central opening 882. Radial extensions 892 may allow insertion of attachment portion 890 into central opening 882, but inhibit retraction from central opening 882. For example, radial extensions 892 may grasp into the interior surface of central opening 882 if coupling portion 856 is pulled proximally relative to attachment portion 890.

In this aspect, actuation member 854 may be a slat or rod with a rectangular cross-section. Actuation member 854 may be advanced distally (arrow K), for example, within guide channel 884, and a distal portion of actuation member 854 may abut or otherwise manipulate a portion of arm 810 or ring portion 864 to urge arm 810 inward toward the longitudinal axis of the insertion device (not shown). In this aspect, arm 810 may pivot inward, for example, about a position near the junction of arm 810 and ring portion 864, and/or a position distal to through-hole 872. Alternatively, actuation member 854 may be retracted proximally, and arm 810 may be allowed to bias outwardly or otherwise return to a neutral position. In these aspects, medical device 802 may help to protect the insertion device and/or to form an atraumatic tip, while also helping to provide a number of angles of approach for one or more end effectors to treat the treatment site.

FIGS. 9A-9F illustrate an alternative example, according to the disclosure. FIGS. 9A-9F illustrate similar elements to medical device 102 shown by 800 added to the reference numbers. A medical device 902 may be coupled to a distal portion of an insertion device (not shown), as discussed above.

FIGS. 9A-9F illustrate portions of medical device 902 in a various configurations. As shown, medical device 902 may include a coupling element 996, for example, at a distal end of medical device 902. Coupling element 996 may be coupled to or otherwise surround a portion of an insertion device (not shown), for example, a distal end of an insertion device. Coupling element 996 may be an annular, ring-shaped element, and coupling element 996 may include a central passage there-through, for example, to receive a portion of the insertion device. In this aspect, coupling element 996 may be friction fit to a distal portion of the insertion device. Moreover, it is noted that coupling element 996 is shown in dashed lines to allow for a clearer representation of other features of medical device 902.

Additionally, medical device 902 includes one or more arm elements 910, tubes 912, a first wire 914A, and a second wire 914B. Arm element 910 may be a block, for example, generally cube or box shaped, and may be formed via a solid extrusion with a number of lumens extending through. Nevertheless, arm element 910 may be any shape to be received within or be positioned adjacent to a portion of coupling element 996. It is noted that FIGS. 9A-9F show a portion of medical device 902 with one set of arm element 910, tube 912, first wire 914A, and second wire 914B, but medical device 902 may include two, three, four, or more sets of arm element 910, tube 912, first wire 914A, and second wire 914B. The sets of arm element 910, tube 912, first wire 914A, and second wire 914B may be evenly positioned about a distal circumference of medical device 902, for example, to be positioned around a distal end of an insertion device.

Figure 9A:
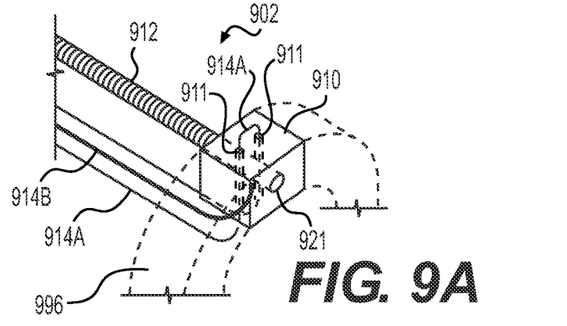
FIGS. 9A-9F illustrate various views of a portion of another exemplary medical device in various configuration, according to aspects of the disclosure.
Figure 9B:
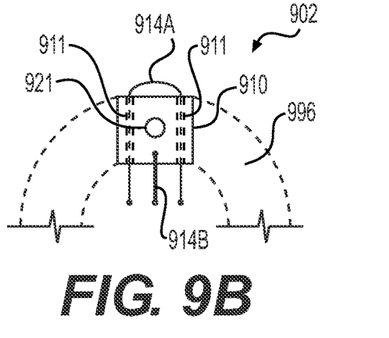

FIG. 9A shows a perspective view of a portion of medical device 902 in a closed configuration, and FIG. 9B shows an end view of the portion of medical device 902 in the closed configuration. Medical device 902 may be in the closed configuration during insertion and/or repositioning of the insertion device (not shown). As shown, arm element 910 is positioned within an opening 998 (FIGS. 9E and 9F) in coupling element 996. Tube 912 is coupled to a proximal portion of arm element 910, and, as discussed herein, arm element 910 includes an arm channel 921 such that an end effector may be delivered through a channel in tube 912 and arm channel 921 to treat the treatment site.

Arm element 910 may include two lumens 911 to receive portions of first wire 914A and to allow arm element 910 to move along first wire 914A. Accordingly, first wire 914A may extend through one lumen 911 of arm element 910 from a first bottom portion to a first top portion, and then through a second lumen 911 from a second top portion to a second bottom portion to form a loop. The first bottom portion and the second bottom portion are spaced apart from each other, and the first top portion and the second top portion are also spaced apart from each other, such that lumens 911 are spaced apart from each other. Therefore, first wire 914A may be movable relative to arm portion 910, and arm portion 910 may be movable relative to first wire 914A. Second wire 914B may be fixedly coupled to a portion of arm element 910. Moreover, as shown in FIGS. 9E and 9F, first wire 914A and second wire 914B may extend through a portion of coupling element 996, for example, through respective lumens or channels.

Figure 9C:
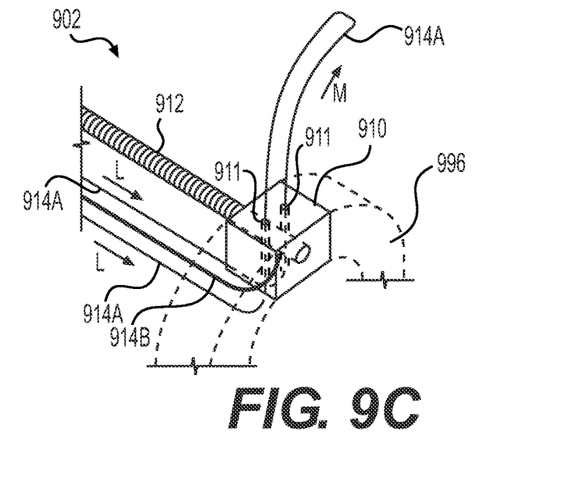
Figure 9D:
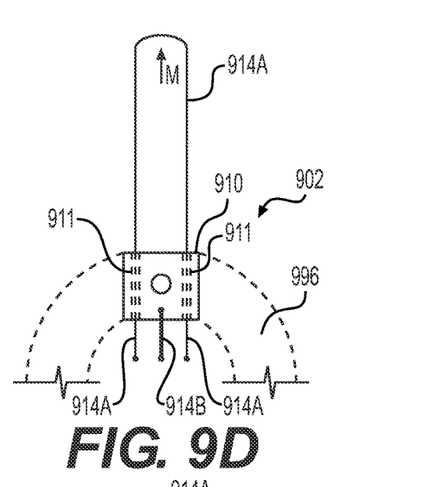

FIG. 9C shows a perspective view of the portion of medical device 902 in an intermediate configuration, and FIG. 9D shows an end view of the portion of medical device in the intermediate configuration. First wire 914A may be advanced or otherwise urged distally (arrow L). Alternatively, first wire 914A may be slackened at a proximal control to allow for first wire 914A to extend distally. Arm element 910, tube 912, and second wire 914B may remain stationary. As shown in FIGS. 9C and 9D, a greater portion of first wire 914A may extend distally beyond arm element 910 than in the closed configuration of FIGS. 9A and 9B, for example, at an angle or curvature relative to arm element 910 (arrow M). The portion of first wire 914A that extends beyond arm element 910 may form a rail or guide for arm element 910. Moreover, the angle or curvature of first wire 914A may be predetermined, for example, by forming first wire 914A out of a shape memory metal or other material. In this aspect, first wire 914A and second wire 914B are separately controllable, for example, via a proximal handle, as discussed above.

Figure 9E:
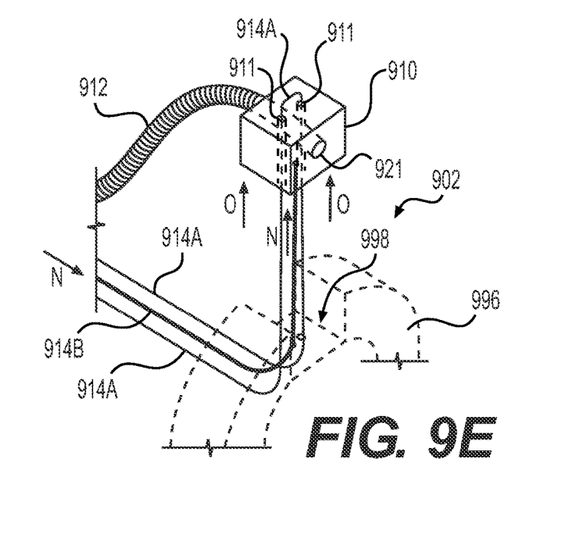
Figure 9F:
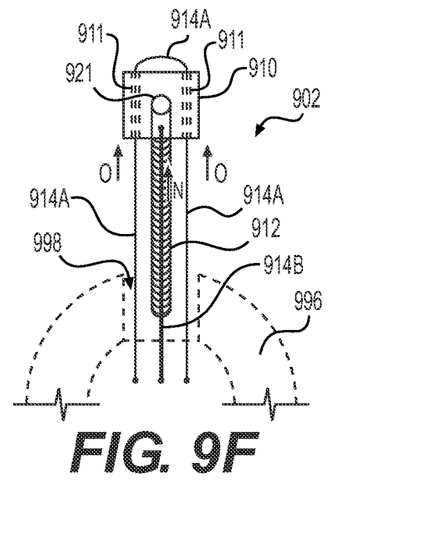

FIG. 9E shows a perspective view of the portion of medical device 902 in an extended configuration, and FIG. 9F shows an end view of the portion of medical device in the extended configuration. Second wire 914B may be advanced or otherwise urged distally (arrow N). Alternatively, second wire 914B may be slackened at a proximal control to allow for second wire 914B to extend distally. First wire 914A may remain stationary. As shown, the movement of second wire 9146 may urge arm element 910, tube 912, and second wire 914B to an extended configuration. For example, arm element 910 may be advanced out of opening 998 and along the rail or guide formed by a portion of first wire 914A (arrow O) that extends beyond arm element 910, such that arm element 910 may follow an angle or curvature of first wire 914A. In this extended position, an end effector may be delivered through tube 912 and out of arm channel 921. Additionally, the extension of first wire 914A and/or second wire 914B may allow the user to control the position of arm element 910 and arm channel 921 relative to an insertion device, treatment site, etc. Furthermore, first wire 914A and second wire 914B may be moved simultaneously to extend and/or retract arm element 910 relative to the insertion device.

As discussed above, medical device 902 may include one or more sets of arm element 910, tube 912, first wire 914A, and second wire 914B, and each set may be transitioned from the closed configuration to the extended configuration, as discussed above. Each set of arm element 910, tube 912, first wire 914A, and second wire 9146 may be controlled together from a proximal handle, or one or more sets of arm element 910, tube 912, first wire 914A, and second wire 914 may be separately controllable. In these aspects, medical device 902 may help to protect the insertion device and/or to form an atraumatic tip, while also helping to provide a number of angles of approach for one or more end effectors to treat the treatment site. Moreover, in some aspects, tube 912 may be formed of or include a spring or coiled wire for greater flexibility, and it is noted that any of the tubes discussed herein may be formed of or includes a spring or coiled wire.

Various aspects discussed herein may allow for an insertion device and a medical device (e.g., medical device 102) to be delivered to a treatment site, for example, to perform endoscopic submucosal dissection ("ESD"). The rounded or otherwise atraumatic shape of a distal portion of medical device 102 may help to deliver the insertion device and the medical device to the treatment site with a reduced likelihood of trauma to the patient. One or more portions of the medical device (e.g., arms 110) may be selectively articulable to expose one or more additional end effectors, a visualization device, an illumination device, etc. Moreover, the selective articulation of one or more portions of the medical device may allow for different angles of approach and/or adjustable and multi-directional tissue lifting or treatment, for example, by one or more end effectors, visualization devices, illumination devices, etc. delivered to the treatment site via tubes 116 and arm tubes 120.

The different angles of approach and/or adjustable multi-directional tissue lifting may be independent of the endoscope (e.g., insertion device 104) during a procedure. Additionally, the medical device may be coupled to the insertion device, so one or more end effectors (e.g., an ESD knife) may be delivered to the treatment site via one or more lumens in the insertion device. A user may thereby deliver one or more end effectors (e.g., a snare) through a first portion of the medical device (e.g., one arm 110) to the treatment site at a first angle in order to capture or otherwise treat tissue or other material, and the user may deliver one or more additional end effectors (e.g., a grasper) through a second portion of the medical device (e.g., another arm 110) to approach the treatment site at a second angle in order to grasp or otherwise treat the tissue or other material. Furthermore, the user may deliver yet another end effector (e.g., a laser fiber) through a third portion of the medical device (e.g., a third arm 110) to approach the treatment site at a third angle in order to cut, mark, or otherwise treat tissue or other material. The end effectors delivered through the medical device may be independently movable, and portions of the medical device (e.g., arms 110) may help stabilize and/or leverage the scope relative to the tissue or other material at or near the treatment site.

One or more other portions of the medical device may help to push, pull, block, or otherwise manipulate and/or stabilize tissue or other material at the treatment site, which may help the user to quickly and safely provide medical treatment at the treatment site. For example, the user may manipulate one portion of the medical device (e.g., one arm 116) to abut and/or push against tissue adjacent to the treatment site in order to provide a more desirable position, orientation, and/or angle of approach to the treatment site for the insertion device or another portion of the medical device (e.g., another arm 116). Furthermore, articulation of one or more portions of the medical device may also help to provide stabilization and/or traction for the medical device at the treatment site, for example, by helping to anchor or otherwise fix a position of the medical device at the treatment site via friction, abutment, or other contact between the medical device and tissue or other material at the treatment site.

Accordingly, various aspects discussed herein may help to improve the efficacy of treatment and/or recovery from a procedure, for example, a removal of a gastrointestinal tumor. Various aspects discussed herein may help to reduce and/or minimize the duration of the procedure, and/or may help reduce risks of inadvertent contact with tissue or other material during delivery, repositioning, or removal of a medical system for the procedure. Additionally, various aspects discussed herein (e.g., medical devices 102, 202, 302, 402, 502, 602, 702, 802, or 902) may be packaged as a kit to be used to treat a patient, for example, by coupling the kit to an insertion device.

While principles of this disclosure are described herein with reference to illustrative aspects for various applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device comprising:
    a longitudinal portion with a plurality of discrete tubes configured to be spaced around an exterior of an endoscope, wherein each tube includes a channel;
    a distal portion with a plurality of arms, wherein each of the arms includes an arm lumen, wherein each arm lumen is connected to a respective channel of a respective tube, wherein the channels and arm lumens are aligned and configured to receive and deliver one or more end effectors out of the arm lumens, and wherein the distal portion is configured to be coupled to an outer surface of a distal end of the endoscope; and
    one or more actuation mechanisms, wherein the one or more actuation mechanisms are movable to transition the plurality of arms from a closed configuration to an open configuration, wherein in the closed configuration, the arm lumens are not exposed from the distal portion, and wherein in the open configuration, the arm lumens are exposed from the distal portion, and wherein the arm lumens are distal of the endoscope in the closed configuration, wherein the arm lumens extend from interior portions of the arms and curve towards a longitudinal axis of the endoscope and are configured to deliver the one or more end effectors to a target treatment site.

2. The medical device of claim 1, wherein the arm lumens have a curvature of approximately 0 to 60 degrees relative to a longitudinal axis of the medical device, when the medical device is in the open configuration.

3. The medical device of claim 1, wherein the plurality of arms include four arms that form a substantially round shape in the closed configuration.

4. The medical device of claim 3, wherein in the closed configuration, the four arms form a central opening at a distal end of the round shape.

5. The medical device of claim 1, wherein each of the one or more actuation mechanisms is one or more wires positioned within a corresponding tube of the plurality of discrete tubes.

6. The medical device of claim 5, wherein the one or more wires are connected to proximal portions of the plurality of arms.

7. The medical device of claim 1, wherein a distal opening of each of the arm lumens faces radially inward in the closed configuration.

8. The medical device of claim 1, wherein the plurality of discrete tubes are surrounded by a sheath.

9. The medical device of claim 1, wherein the plurality of arms are biased to the closed configuration.

10. The medical device of claim 1, wherein in the open configuration, the arm lumens extend further radially outward in the open configuration than in the closed configuration.

11. The medical device of claim 1, wherein the plurality of arms comprise metal or plastic.

12. A medical system comprising:
an endoscope including one or more lumens; and
a medical device coupled to a distal end of the endoscope via a connection portion of the medical device,
wherein the medical device further includes one or more arms at a distal end of the medical device, one or more tubes connected to a proximal end of each of the one or more arms and spaced around an exterior of the endoscope, and one or more wires passing through the one or more tubes and connected to a portion of each of the one or more arms,
wherein movement of the one or more wires transitions the one or more arms from a first configuration to a second configuration, wherein the one or more arms extend farther radially outward away from a longitudinal axis of the endoscope in the second configuration than in the first configuration, wherein each of the one or more tubes includes a first channel configured to receive one or more end effectors,
wherein a distal end of each of the one or more tubes and the proximal end of each of the one or more arms are connected to the connection portion in the first configuration and in the second configuration, and wherein arm lumens are distal of the endoscope in the first configuration, wherein, in the first configuration, the arm lumens are not exposed from a distal portion of the medical device, wherein the arm lumens extend from interior portions of the arms and curve towards a longitudinal axis of the endoscope and are configured to deliver the one or more end effectors to a target treatment site.

13. The medical system of claim 12, wherein the connection portion is ring-shaped.

14. The medical system of claim 12, wherein each of the one or more arms is pivotally connected to the connection portion.

15. The medical system of claim 12, wherein each of the one or more tubes further includes a second channel configured to receive the one or more wires.

16. The medical system of claim 12, wherein the one or more tubes includes a plurality of tubes spaced around an exterior of the endoscope.

17. A medical system comprising:
an endoscope; and
a medical device having:
a longitudinal portion with a plurality of discrete tubes spaced around an exterior of the endoscope,
a distal portion with a plurality of arms, wherein each of the arms includes an arm lumen, wherein each arm lumen is connected to a respective tube,
a ring-shaped connection member configured to couple both the longitudinal portion and the distal portion to the exterior of the endoscope, and
one or more actuation mechanisms, wherein the one or more actuation mechanisms are movable to transition the plurality of arms from a closed configuration to an open configuration, wherein the plurality of arms are pivotally connected to the connection member, wherein arm lumens are distal of the endoscope in the closed configuration, wherein, in the closed configuration, the arm lumens are not exposed from the distal portion, wherein the arm lumens extend from interior portions of the arms and curve towards a longitudinal axis of the endoscope and are configured to deliver one or more end effectors at an angle of approach different from an angle of the plurality of discrete tubes to a target treatment site.

18. The medical system of claim 17, wherein the one or more actuation mechanisms include one or more wires movable within channels of the plurality of discrete tubes.

19. The medical system of claim 17, wherein the connection member connects distal ends of the plurality of discrete tubes and proximal ends of the plurality of arms to one another.

20. The medical system of claim 17, wherein in the open configuration, the arm lumens extend further radially outward in the open configuration than in the closed configuration.

* * * * *